United States Patent [19]
Wilson et al.

[11] Patent Number: 5,330,915
[45] Date of Patent: Jul. 19, 1994

[54] PRESSURE CONTROL SYSTEM FOR A BIOREACTOR

[75] Inventors: John R. Wilson, Minneapolis, Minn.; Ewald Kowol, Fernwald, Fed. Rep. of Germany

[73] Assignees: Endotronics, Inc., Minneapolis, Minn.; Tecnomara Deutschland GmbH, Fernwald, Fed. Rep. of Germany

[21] Appl. No.: 779,082

[22] Filed: Oct. 18, 1991

[51] Int. Cl.⁵ .............. C12M 1/36; C12M 1/04; C12M 3/04
[52] U.S. Cl. ............................. 435/289; 435/285; 435/313
[58] Field of Search ............ 435/3, 284, 289, 291, 435/313, 285; 422/112, 115

[56] References Cited

U.S. PATENT DOCUMENTS

| | | | |
|---|---|---|---|
| 4,201,845 | 5/1980 | Feder et al. | 435/285 |
| 4,636,473 | 1/1987 | Kleinstreuer | 435/291 |
| 4,720,462 | 1/1988 | Rosenson | 435/285 |
| 4,722,902 | 2/1988 | Harm et al. | 435/284 |
| 4,889,812 | 12/1989 | Guinn et al. | 435/289 |
| 4,973,558 | 11/1990 | Wilson et al. | 435/291 |
| 4,999,298 | 3/1991 | Wolfe et al. | 435/289 |

FOREIGN PATENT DOCUMENTS

| | | | |
|---|---|---|---|
| 0419234 | 3/1991 | European Pat. Off. | 435/284 |
| 00188 | 1/1989 | World Int. Prop. O. | |
| 8911529 | 11/1989 | World Int. Prop. O. | 435/285 |
| 9013639 | 11/1990 | World Int. Prop. O. | 435/284 |

*Primary Examiner*—Robert J. Warden
*Assistant Examiner*—T. A. Trembley
*Attorney, Agent, or Firm*—Sughrue, Mion, Zinn, Macpeak & Seas

[57] ABSTRACT

A pressure control system for a bioreactor of the type having a gas space and a cell culture space therein is supplied with a gas such as oxygen separately from the supply of liquid nutrient media. The pressures in the gas space and the pressure in the cell culture space are controlled so that a higher pressure is maintained in the cell culture space than in the gas space to prevent displacement of the liquid nutrient media.

6 Claims, 5 Drawing Sheets

PRESSURE CONTROL SYSTEM FOR A BIOREACTOR

BACKGROUND OF THE INVENTION

The present invention is directed to a control system for a bioreactor and more specifically to a method and apparatus for controlling the pressures in a bioreactor to prevent displacement of the livid medium in the cell growth space of a bioreactor.

The culturing of living cells in vitro is performed for a variety of purposes including the preparation of viral vaccines, the recovery of valuable hi-products of cell metabolism and the production of tissue-like derivatives for creating artificial organs.

One method of growing living cells in vitro, which is well known in the art, is hollow fiber technology. Hollow fiber technology provides advantages such as high product concentration, purity and high cell density.

As with all in vitro bioreactors, oxygenation of the cells is a major obstacle to effective and efficient utilization of the cell space.

Traditional hollow fiber methods of providing oxygen to the cells have been to oxygenate liquid medium prior to its delivery to the intercapillary side of the hollow fiber. Oxygen then transfers via diffusion across the fiber wall to the cell environment. This method of delivery is hampered by the fact that aqueous medium, equilibrated with air, can only carry 0.2 mMol of oxygen per liter (37° C., 760 mm Hg). Thus, a large volume of medium must be delivered to the bioreactor to provide a relatively small amount of oxygen.

In accordance with the increasing oxygen requirements of a growing culture, the delivery rates of the oxygenated medium increase. This leads to associated mechanical and biological difficulties as pumps, tubing, fittings in addition to the bioreactor and the medium itself, become subjected to increased pressure and velocity.

A hollow fiber type bioreactor which addresses these problems is constructed in such a way as to allow oxygen to be delivered to the cell environment independently of the medium flow rate.

A hollow fiber-type device which provides for separate oxygen and nutrient media delivery to the cells is disclosed in U.S. Pat. No. 5,079,168 granted Jan. 7, 1992 entitled CELL CULTURE APPARATUS and assigned to Endotronics, Inc. which is a co-Assignee of the present application. This cell culture device is comprised of at least one envelope comprised of first and second membrane layers which are porous and substantially permeable to gases but substantially impermeable to cells and liquids. The envelope is spirally wrapped about an elongated core to define a spirally extending inter-envelope gas space therebetween. Suitable means are provided for delivering nutrient media and cells to the cell culturing space and additional means are provided for delivering a gas to the cell culturing space through the first and second membrane layers. Suitable removal means are also provided for removing liquid metabolic waste products and cell products from the cell culturing space and for removing gaseous waste products from the cell culturing space through the first and second membrane layers.

Another hollow fiber-type device which provides for separate oxygen and nutrient media delivery to cells is also disclosed in co-pending U.S. patent application Ser. No. 07/717,600 filed Jun. 19, 1991, now abandoned entitled CELL CULTURE APPARATUS, which is also assigned to Endotronics, Inc. In this hollow fiber-type device first and second membrane sheets are sealed to each other along their edges to define an envelope with a cell culturing space therebetween. The first and second membrane sheets are porous and substantially permeable to gases but substantially impermeable to cells and liquids. The envelope is disposed between upper and lower rigid plates which form a housing to retain the envelope. A plurality of such envelopes may be stacked within the housing with the housing defining an inter-envelope gas space for the delivery of gas to the cell culturing space through the porous membranes. Suitable delivery means are provided for delivering nutrient media and cells to the cell culturing space and for delivering gas to the inter-envelope gas space. Suitable removal means are also provided for removing metabolic waste products and cell products from the cell culturing space and for removing gaseous waste products from the inter-envelope space.

While the use of gas permeable membranes in direct contact with the cell environment is a highly efficient method of oxygenating cells, the supporting cultureware must be tailored to address problems inherent to this type of bioreactor.

Specifically, the pressure of the cell environment side of the gas permeable membrane must exceed the pressure on the gas side of the gas permeable membrane. If this condition is not maintained, gas will drive across the gas permeable membrane, displacing the cell environments liquid medium and eventually killing the culture. The present invention does not allow this condition to occur.

Additional advantages accrue from utilizing a bioreactor having gas permeable membranes in direct contact with the cell environment as opposed to oxygenating the liquid media being supplied to the bioreactor. Since there is no need to oxygenate the liquid medium entering the bioreactor, flow rates are commensurate with the nutrient delivery needs and waste removal requirements. The systems described in the present application supplies liquid medium directly to the bioreactor simplifying the cultureware complexity and reducing cost.

A problem that results from the elimination of the medium storage vessels is related to the decreased gas solubility of the medium as the temperature of the medium rises. More specifically, the medium is often refrigerated to maintain its life. As it enters the incubator, it increases in temperature and outgasses creating bubbles in the medium. Normally, these would be vented in an intermediate storage vessel, but the direct feed method, according to the present invention, does not permit venting of the bubbles. Thus, the bubbles could form an air lock in the medium delivery path or portions thereof within the bioreactor. The present invention does not allow this condition to occur.

SUMMARY OF THE INVENTION

The present invention provides a new and improved system for controlling relative pressures within a hollow fiber-type bioreactor to prevent displacement of the cell culturing space aqueous medium by gas.

The present invention provides a new and improved pressure control system for a bioreactor wherein the cell culturing space pressure exceeds the surrounding gas space pressure in order to keep the cell culturing space from being displaced by air.

The present invention also provides a new and improved pressure control system for a bioreactor wherein the pressure of the liquid cell space is maintained positive relative to the pressure of the surrounding gas space by means of a positive pressure mechanism applied to the medium tubing.

The present invention provides a means of unsolubilized gas removal from the aqueous medium delivered to the bioreactor.

The foregoing and other objects, features and advantages of the invention will be apparent from the following more particular description of a preferred embodiment of the invention as illustrated in the accompanying drawings.

DETAILED DESCRIPTION OF THE INVENTION

The use of gas permeable membranes in direct contact with the cell environment of a bioreactor is a highly efficient method of oxygenating cells. However, in such bioreactors, the cell culturing space must be maintained at a pressure in excess of the pressure in the gas space in order to prevent the cell space from being displaced by the gas pressure. This type of bioreactor is shown schematically in FIGS. 3 and 4.

Figure 3:
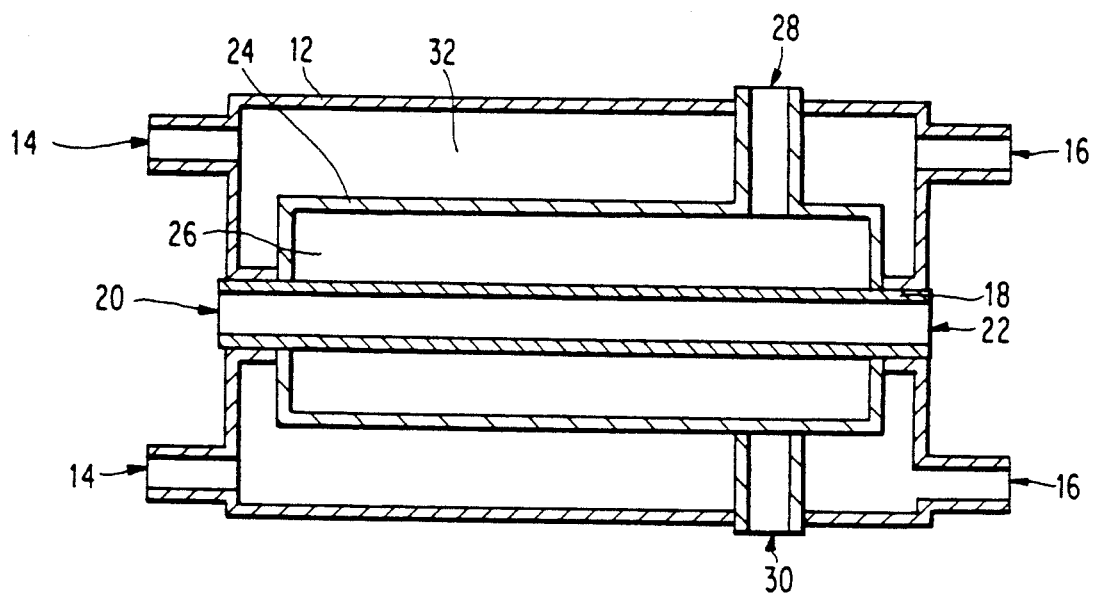
FIG. 3 is a schematic cross-sectional view of a first type of bioreactor with a gas inlet and gas outlet separate from a medium inlet and a medium outlet.

In the bioreactor shown in FIG. 3, the rigid bioreactor case 12 is provided with a pair of gas inlets 14 and a pair of gas outlets 16 for supplying oxygen to the bioreactor and removing gaseous waste products. At least one hollow tubular passage 18 extends through the bioreactor case 12 with the inlet 20 being disposed intermediate the gas inlets 14 and the outlet 22 being disposed intermediate the gas outlets 16. A hydrophobic gas permeable membrane defines an envelope 24 completely surrounding the hollow tubular passage in spaced relation thereto to define a cell culture space 26. The cell culture space 26 is provided with an inlet passage 28 for the introduction of cells to the cell culturing space and an outlet 30 for the harvesting of cells and/or cell secreted products.

The envelope 24 is formed from hydrophobic material which is porous and substantially permeable to gases but substantially impermeable to cells and liquids. The hollow tubular passage member 18 is constructed from a hydrophilic membrane which is semi-permeable, permitting the passage of nutrients from the nutrient media into the cell culturing space 26 and permitting the removal of waste products from the cell culturing space to the media for discharge through the outlet 22. Since the hydrophobic material of the envelope 24 is not rigid and has little structural strength, it is necessary to maintain the pressure within the cell culturing space 26 higher than the pressure within the gas space 32 in order to prevent displacement of the liquid medium in the cell growth space of the bioreactor.

The bioreactor shown schematically in FIG. 3 is very similar in principle to the cell culture apparatus disclosed in co-pending U.S. patent application Ser. No. 07/717,600 now abandoned identified above.

Figure 4:
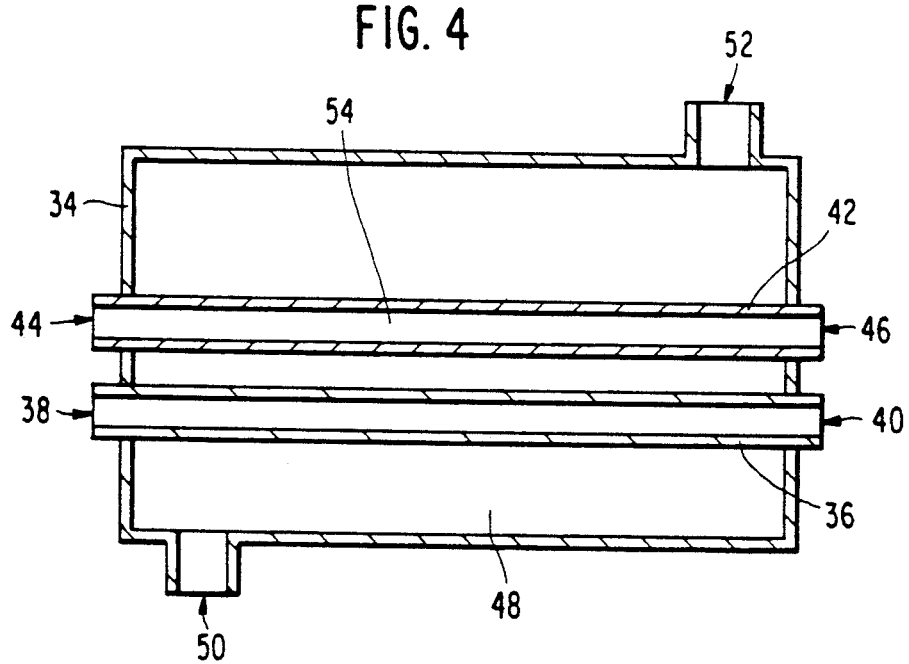
FIG. 4 is a schematic cross-sectional view of a second type of bioreactor with a gas inlet and gas outlet separate from a medium inlet and a medium outlet.

The system according to the present invention can also be used with a bioreactor of the type shown schematically in FIG. 4, wherein the substantially rigid bioreactor case 34 is provided with at least one hollow tubular passage 36 of hydrophilic material having a nutrient media inlet 38 and a media outlet 40. At least one additional hollow tubular passage member 42 extends through the casing 34 parallel to the member 36. The hollow tubular passage member 42 is constructed of hydrophobic, gas permeable material and is provided with a gas inlet 44 and a gas outlet 46. The entire space within the casing 34 surrounding the tubular members 36 and 42 defines the cell culturing space 48. The cell culturing space 48 is provided with an inlet 50 for the introduction of a liquid media and cells and an outlet 52 for the harvesting of cells and/or cell secreted product. As in the previous embodiment shown in FIG. 3, the pressure in the cell culturing space 48 must be higher than the pressure within the gas space 54 to prevent the displacement of the liquid medium in the cell growth space by gas.

Figure 1:
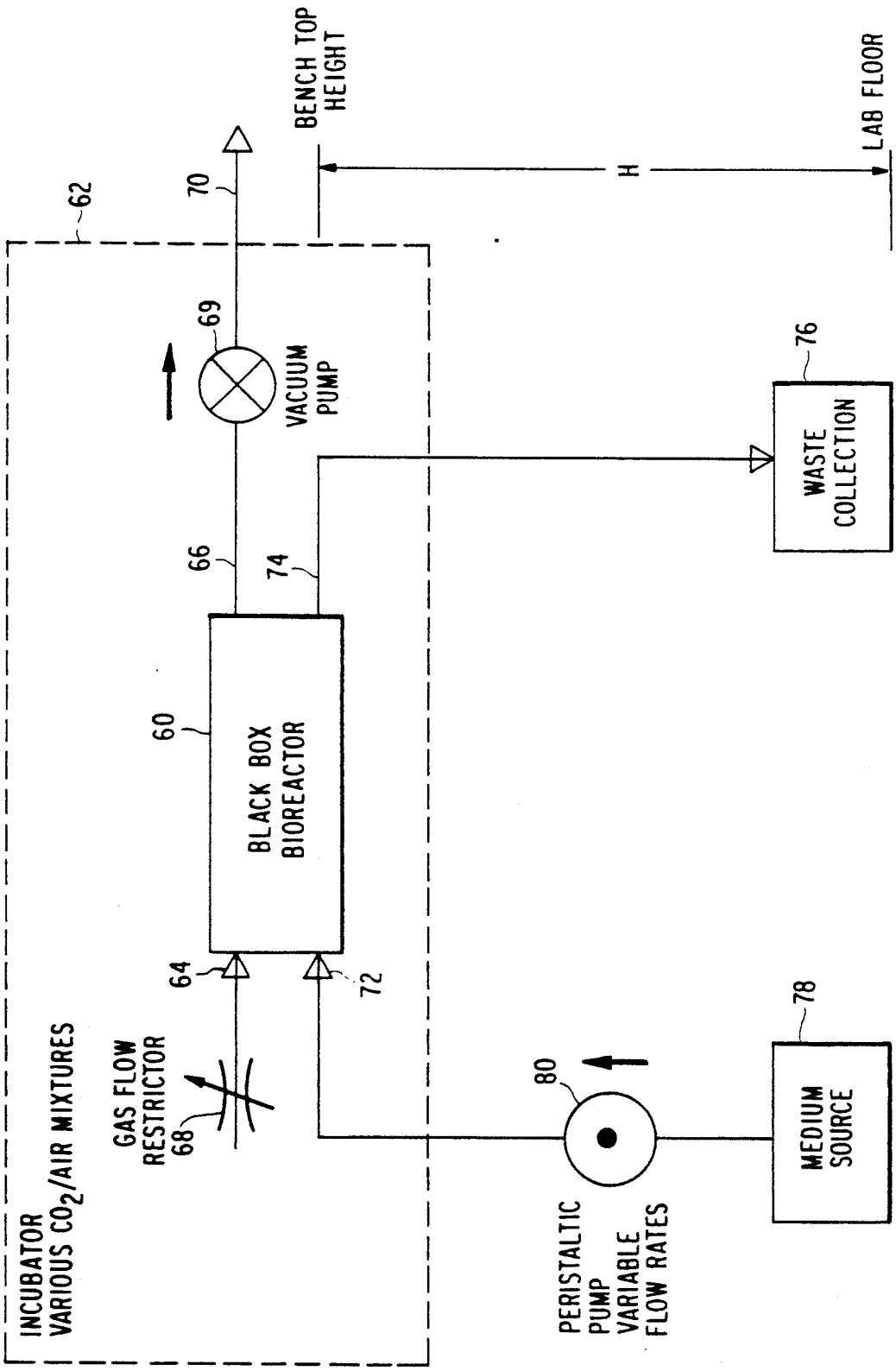
FIG. 1 is a schematic diagram of a negative pressure system for a bioreactor according to a first embodiment of the present invention.

The relative pressures in the cell growth space and the gas space can be controlled in accordance with a negative pressure control system as shown in FIG. 1. The bioreactor 60 of the type shown in FIGS. 3 and 4 or of the type shown in the two above identified co-pending applications, is disposed within a conventional incubator 62 which contains various $CO_2$/air mixtures at the desired temperatures. The bioreactor is provided with a gas inlet 64 and a gas outlet 66. The gas flow restricter 68 is connected to the gas inlet and a vacuum pump 69 is connected between the gas outlet 66 and an exhaust pipe 70 extending externally of the incubator 62. The bioreactor 60 is also provided with the nutrient media inlet 72 and an outlet 74 connected to a waste collection vessel 76 disposed at a distance H below the bioreactor 60. The nutrient media is supplied from a medium source 78 to the inlet 72 by means of a peristaltic pump 80 capable of producing variable flow rates. According to this system, it is desirable to reduce the pressure of the gas space within the bioreactor below the pressure of the cell cultivating space within the bioreactor. The cell space within the bioreactor will be at a negative gauge pressure since the waste collection vessel is located at a lower level than the bioreactor and removes the media by means of a syphon effect. The quantitative value of the negative gauge pressure in the cell cultivating space will be directly proportional to the distance H between the bioreactor 60 and the waste collection vessel 76.

The gas flow restricter 68 in combination with the vacuum pump 69, will place the gas space at a pressure value below that generated by the syphon effect. Typical pressures will be −60 mm Hg syphon and −120 mm Hg gas space. The gas restricter will serve the additional purpose of controlling gas flow rates to ensure that evaporation of liquid across the hydrophobic membrane within the bioreactor is limited to a value which will not generate dangerous osmolarity conditions.

Figure 2:
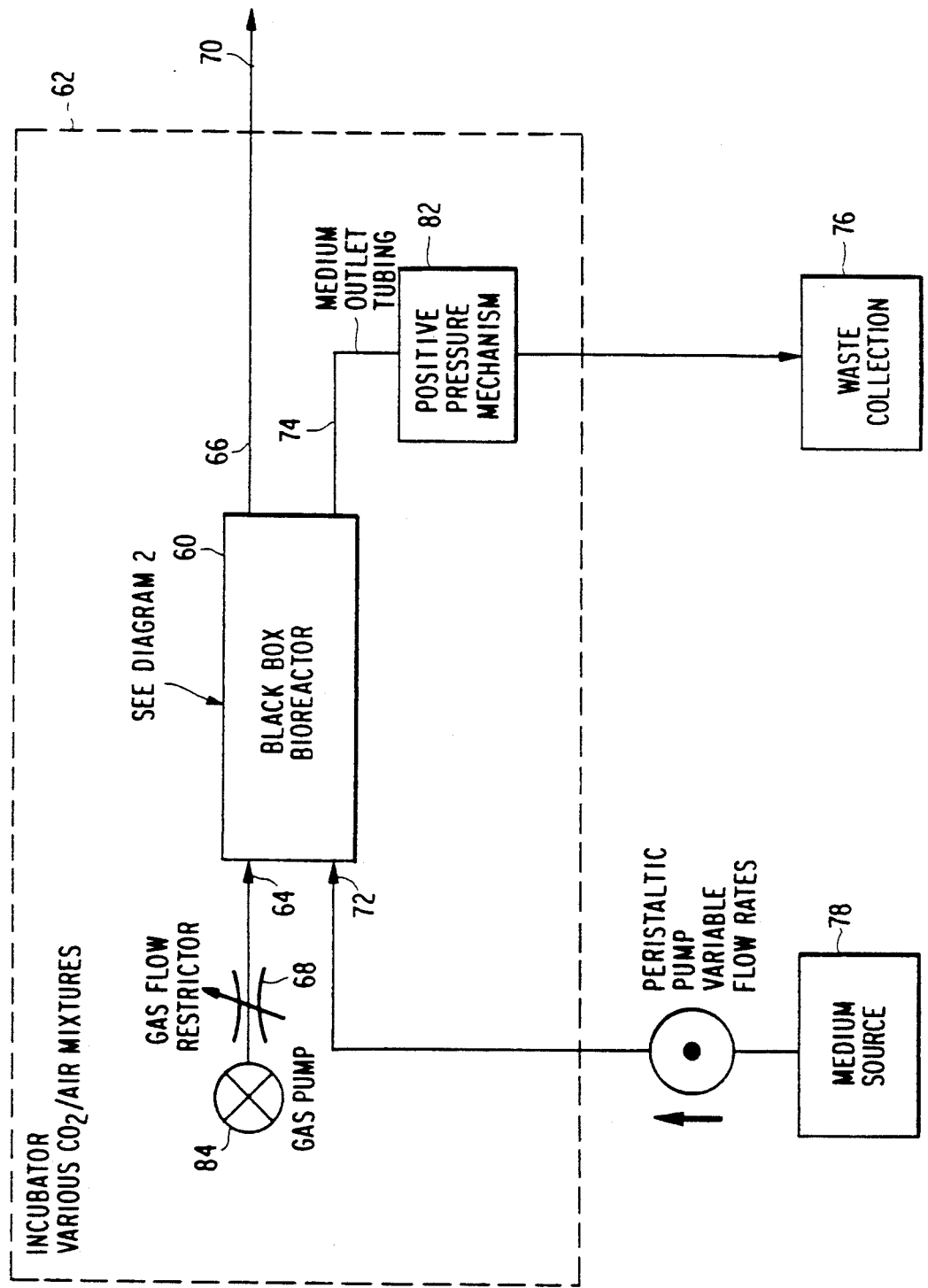
FIG. 2 is a schematic diagram of a positive pressure system for a bioreactor according to a second embodiment of the present invention.

In the embodiment shown in FIG. 2, a positive pressure system is utilized to prohibit the liquid medium in the cell space of the bioreactor from being displaced by the gas. As in the previous embodiment, the bioreactor 60 is located within an incubator 62 and the bioreactor is provided with a gas inlet 64, a gas outlet 66, a nutrient media inlet 72, and a media outlet 74. Nutrient media is delivered from a media source 78 by means of a peristaltic pump 80 to the nutrient inlet 72. However, a positive pressure device 82 is connected between the media outlet 74 and the waste collection vessel 76. The positive pressure device 82 is designed to selectively restrict the media flow from the bioreactor to cause the pressure of the cell cultivation space within the bioreactor to be higher than the pressure of the surrounding gas space. In the embodiment of FIG. 2, gas pump 84 supplies the gas to the inlet 64 through a gas flow restricter 68 so that the pressure in the gas space will be less than the pressure within the cell cultivation space.

Figure 5:
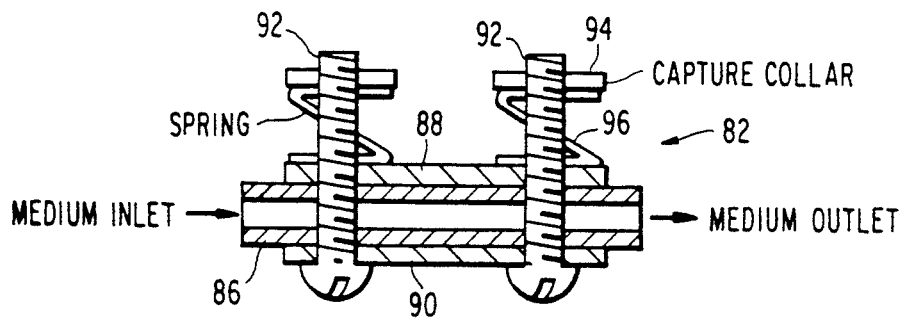
FIG. 5 is a schematic cross-sectional view of a flow restricter for a medium flow according to a first embodiment of the present invention.

A suitable positive pressure device 82 is shown in FIG. 5 for restricting the flow of the media from the bioreactor. The media outlet 74 from the bioreactor is in the form of a flexible tube 86 in the vicinity where it passes through the positive pressure device 82. The flexible tube 86 is disposed between two parallel plates 88 and 90 having a plurality of holes through which a plurality of threaded bolts 92 extend on opposite sides of the tube 86. A nut 94 is threaded on each bolt and a spring 96 is disposed between each nut and the plate 88. The pressure exerted by the springs 96 can be adjusted by rotating the nuts 94 relative to the bolts 92 so as to vary the pressure exerted on the tube 86 by the opposed plates 88 and 90. The greater the spring pressure, the greater the restriction of the tubing 86 so as to restrict the flow of media through the tube.

Figure 6:
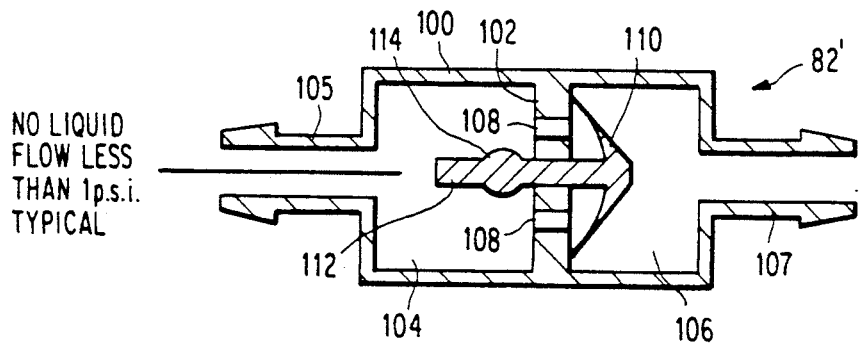
FIG. 6 is schematic cross-sectional view of a flow restricter for a medium flow according to a second embodiment with the valve in the closed position.
Figure 7:
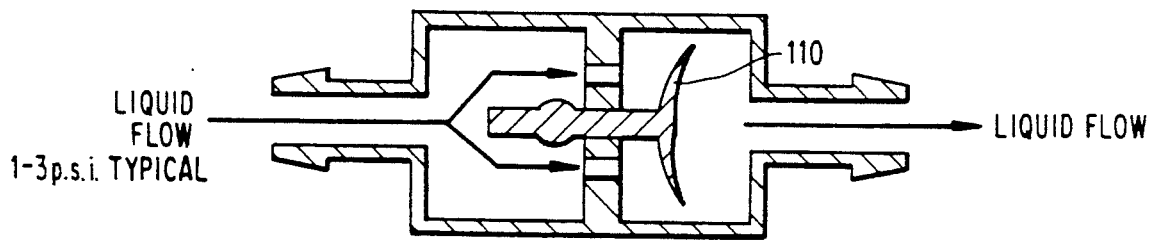
FIG. 7 is a view similar to FIG. 6 but with the valve in the open position.

A second embodiment of a positive pressure device 82' is shown in FIG. 6. The device 82' is comprised of a valve body 100 having an internal dividing wall 102 which divides the center of the valve body into an inlet chamber 104 and an outlet chamber 106. The inlet chamber 104 is provided with an inlet passage 105 adapted to be connected to the media outlet tube 74 leading from the bioreactor 60. Outlet chamber 106 is provided with an outlet passage 107 adapted to be connected to a suitable tube leading to the waste collection vessel 76. The intermediate dividing wall 102 is provided with a plurality of through passages 108 and a flexible valve member 110 overlies the passages 108 within the outlet chamber 106. The valve stem 112 connected to the valve member 110 extends through the dividing wall 102 and is provided with an enlargement 114 to prevent movement of the valve stem to the right as shown in FIGS. 6 and 7. In FIG. 6 the valve member 110 closes the passages 108 when the pressure within the cell culturing space is less than some specified pressure (typically 1 psi). When the pressure (typically exceeds the specified opening pressure within the range of 1-3 psi), the valve member 110 will move to the open position as shown in FIG. 7 to permit the flow of liquid through the valve body. Thus both of the positive pressure devices 82 and 82' are capable of maintaining a suitable pressure within the cell culture space of the bioreactor which will be greater than the pressure in the gas space. The gas flow restricter 68 is adjustable to ensure a sufficiently low positive pressure within the gas space.

Figure 8:
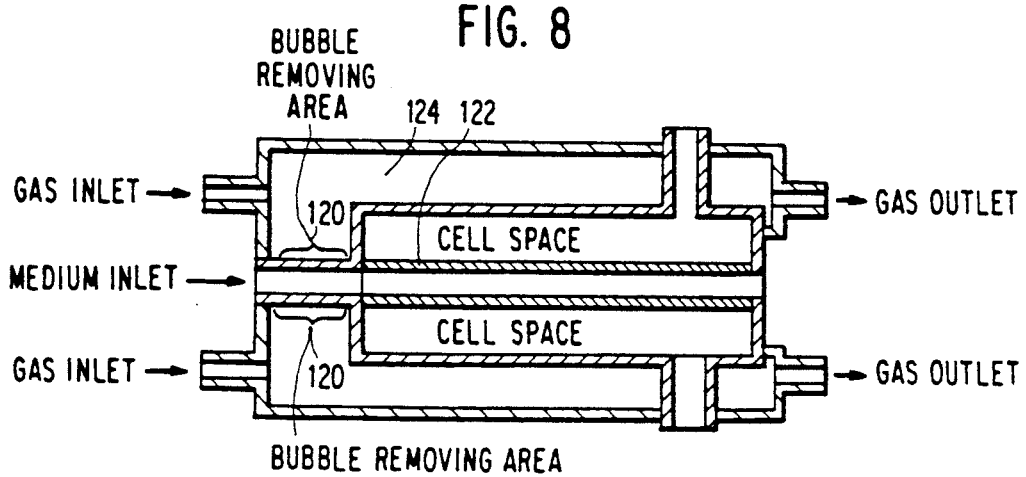
FIG. 8 is a schematic cross-sectional view of a bioreactor similar to the bioreactor of FIG. 3 with the medium inlet modified to be disposed directly in contact with the gas space.

Utilizing a bioreactor having gas permeable membranes provides an additional advantage of eliminating intermediate medium storage vessels common to most perfusion technologies that utilize hollow fibers or sheet permeable membranes. The system described in the present application provides for removal of unsolubilized gas accruing in the liquid medium as a result of increasing temperatures. This is accomplished by bringing the portion 120 of the medium supply tube 122 into contact with the gas space 124 as shown in FIG. 8. Bubbles in the medium pass through the portion 120 of the medium supply tube into the gas space within the bioreactor.

Figure 9:
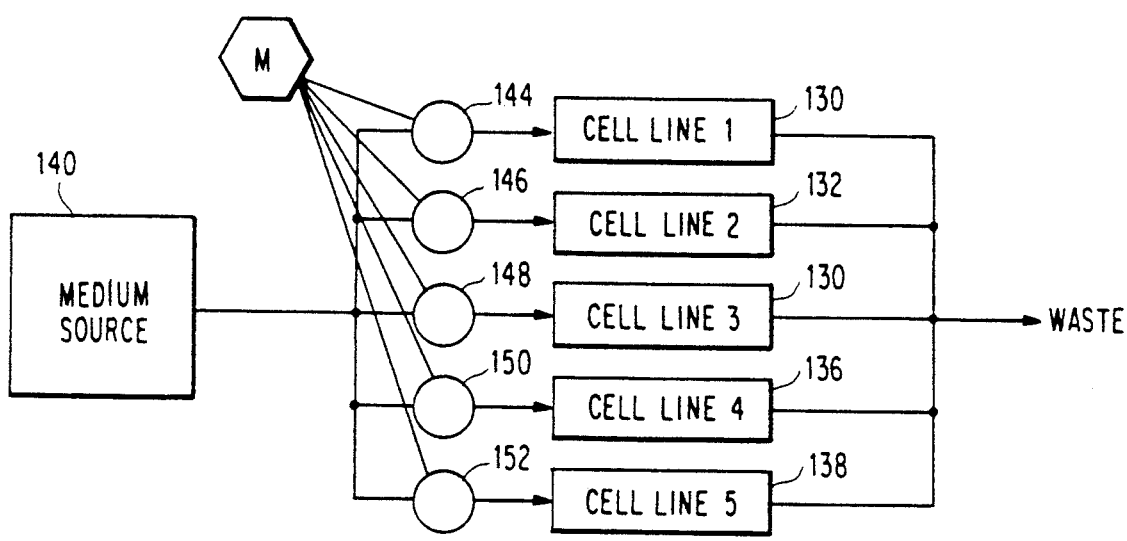
FIG. 9 is a schematic diagram of a system for analyzing five separate cell lines with a common culture medium.
Figure 10:
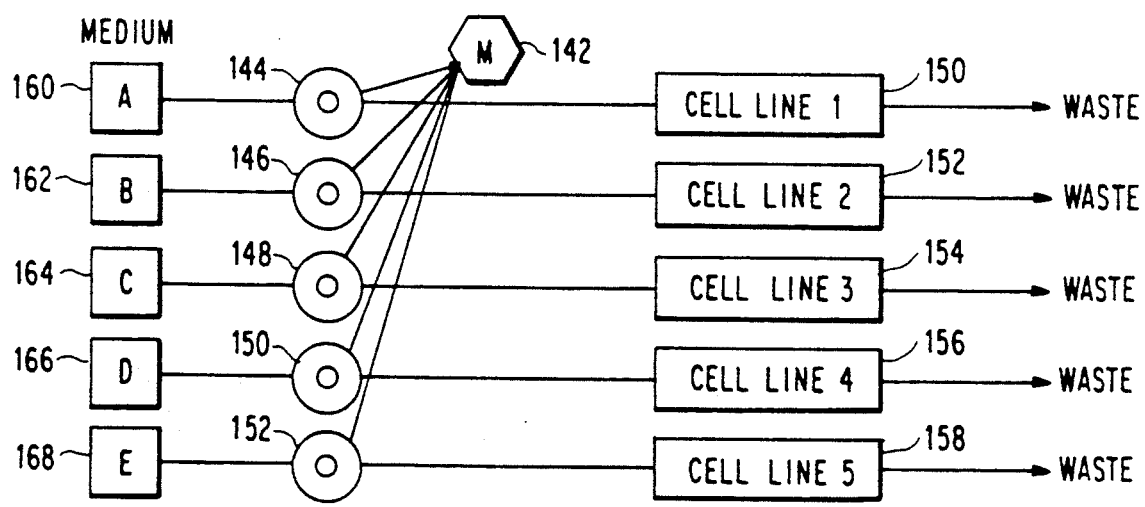
FIG. 10 is a schematic diagram view of a system for analyzing multiple similar cell lines with different culture mediums.

An additional advantage of having separate gas delivery and medium delivery to the bioreactor is illustrated in FIGS. 9 and 10. In FIG. 9, five separate cell lines 130, 132, 134, 136 and 138, are supplied with a culture medium from a common source 140. A single motor 142 can be provided for driving individual pumps 144, 146, 148, 150 and 152 associated with each cell line. Likewise, five equivalent or similar cell lines 150-158 can be analyzed with five different culture mediums and five different sources 160-168. Once again, a common motor 142 is used to drive five individual pumps 144-152 connected between each medium source and cell line respectively.

While the invention has been particularly shown and described with reference to preferred embodiments thereof, it will be understood by those in the art that the foregoing and other changes in form and details may be made therein without departing from the spirit and scope of the invention.

What is claimed is:

1. A pressure control system for a bioreactor comprising:

a bioreactor having a gas space and a cell culture space therein separated by a hydrophobic gas permeable membrane which is impermeable to cells and liquids;

gas supply means and gas removal means connected to a gas inlet and a gas outlet, respectively, of said gas space in said bioreactor;

liquid nutrient media supply means and liquid waste removal means connected to said bioreactor separately from said gas supply means and gas removal means; and gas pressure control means for controlling the gas pressure in said gas space and liquid nutrient media pressure control means for controlling pressure in said cell culture space being operatively connected to said bioreactor to maintain a higher pressure in said cell culture space than in said gas space to prevent displacement of the liquid media in the cell culture space.

2. A pressure control system for a bioreactor as set forth in claim 1;

wherein said gas supply means includes a gas flow restrictor connected to said gas inlet of said gas space and said gas removal means is comprised of a vacuum pump connected to said gas outlet of said gas space for creating a specific pressure level in said gas space; and wherein said liquid nutrient media supply means is comprised of a media source and pump means and said liquid waste removal means is comprised of waste collection means disposed below said bioreactor for producing a syphon flow of liquid waste from said bioreactor to provide a reduced pressure in said cell culture space;

whereby gas pressure is reduced as gas flows across said gas flow restrictor such that the gas pressure is less than the reduced pressure in said cell culture space.

3. A pressure control system for a bioreactor as set forth in claim 1;

wherein said gas supply means is comprised of a gas pump and a gas flow restricter connected in a series with said bioreactor; and wherein said liquid nutrient media supply means is comprised of a media source and pump means connected in series to said bioreactor and said waste removal means is comprised of a liquid flow restriction means in series with a waste collection vessel.

4. A pressure control system for a bioreactor as set forth in claim 3, wherein said liquid flow restriction means is comprised of a flexible tube for carrying said liquid waste and an adjustable spring biased clamping means engaging said flexible tube to selectively restrict the flow therethrough in order to adjust the pressure within said cell culture space.

5. A pressure control system for a bioreactor as set forth in claim 3, wherein said liquid flow restricting means is comprised of flexible one way valve means connected to an outlet tube leading from said bioreactor.

6. A pressure control system as set forth in claim 1, wherein said liquid nutrient media supply means includes passage means in said bioreactor with said passage means having a first portion in direct contact with said gas space to permit transfer of bubbles entrapped in said liquid nutrient media to pass into said gas space and a second portion in contact with said cell culture space.

* * * * *